United States Patent [19]

Boross et al.

[11] Patent Number: 4,593,004

[45] Date of Patent: Jun. 3, 1986

[54] PROCESS FOR THE IMMOBILIZATION OF CYCLODEXTRINE GLYCOSYLTRANSFERASE ENZYME

[75] Inventors: László Boross; Iván Daróczi; Katalin Ivony nee Kaldive, all of Budapest; Gábor Seres, Halásztelek; Béla Szanjáni; József Szejtli, both of Budapest, all of Hungary

[73] Assignee: Reanal Finomvegyszergyar, Budapest, Hungary

[21] Appl. No.: 526,034

[22] Filed: Aug. 24, 1983

[30] Foreign Application Priority Data

Aug. 24, 1982 [HU] Hungary ............................ 2716/82

[51] Int. Cl.$^4$ ...................... C12N 11/06; C12N 11/02; C12N 11/10; C12N 11/08
[52] U.S. Cl. ................................. 435/181; 435/177; 435/178; 435/179; 435/180
[58] Field of Search ............... 435/177, 178, 179, 180, 435/181

[56] References Cited

U.S. PATENT DOCUMENTS 4,338,398  7/1982  Yoneyama ............................ 435/95
4,525,457  6/1985  Sakata et al. ......................... 435/178

OTHER PUBLICATIONS

Zaborsky, O. *Immobilized Enzymes,* CRC Press, Cleveland, Ohio, 1973 (pp. 26–27).

Biotechnol. Bioeng. 19, pp. 87–99, Nakamura et al. (1977).

*Primary Examiner*—Robert J. Warden
*Assistant Examiner*—Patricia Kate White
*Attorney, Agent, or Firm*—Karl F. Ross; Herbert Dubno

[57] ABSTRACT

The invention relates to a process for the preparation of a cyclodextrine glycosyltransferase enzyme.

The immobilization can be carried out by two methods. According to the first method a cyclodextrine glycosyltransferase enzyme is activated with a solution of a carbodiimide compound and the thus treated enzyme is applied in a solution having a pH value of 4.5–8.5 onto a polysaccharide derivative comprising at least 0.1 m-equiv./g of free amino group. According to the second method the enzyme is applied in a solution having a pH value of 4.5–8.5 onto a polymer produced from an acrylic acid and/or methacrylic acid or acrylic amide and/or methacrylic amide monomer by means of a cross-linking agent of the acrylic or allylic type which polymer comprises at least 0.1 m-equiv./g of functional carboxy group, activating the polymer with a solution of a carbodiimide compound and washing and if desired drying the product thus obtained.

The advantage of the process of the present invention is that the thus immobilized enzyme—contrary to the dissolved enzyme—is suitable for longlasting application and can be readily used on industrial scale continuous production.

12 Claims, No Drawings

PROCESS FOR THE IMMOBILIZATION OF CYCLODEXTRINE GLYCOSYLTRANSFERASE ENZYME

FIELD OF THE INVENTION

This invention relates to the immobilization of the enzyme cyclodextrin glycosyltransferase.

BACKGROUND OF THE INVENTION

As a result of the treatment of partially hydrolyzed starch with cyclodextrin glycosyltransferase enzyme (referred to hereinafter as CGTase) molecular rings consisting of 6, 7 and 8 glucopyranose units, respectively are formed (i.e. the so-called cyclodextrins, namely $\chi$-, $\beta$- and $\gamma$-cyclodextrin) which are capable of including molecules of other substances. This so-called "molecular encapsulation" can be used for the improvement of the properties of certain sensitive, volatile, easily oxidizable or poorly soluble substances.

According to prior art, only batch-wise procedures are known for the use of dissolved CGTase. In continuous processes the enzyme is immobilized on a solid phase carrier. According to Biotechnol. Bioeng. 19, 87 (1977) the succinated form of CGTase can be immobilized on a vinyl pyridine copolymer anion exchanger through ionic bonds. In this case although the preliminary succination increases the strength of the bond, the gradual desorption of the enzyme still takes place. This desorption can be avoided by binding the enzyme through covalent bonds to the carrier because this leads to the formation of a new solid phase catalyst which preserves the catalytic activity of the enzyme and is less sensitive to the reaction conditions.

OBJECT OF THE INVENTION

The object of the present invention is to provide CGTase immobilized on a solid phase carrier through covalent bonds.

DESCRIPTION OF THE INVENTION

According to the present invention there is provided an immobilized CGTase enzyme composition suitable for longlasting use in which the enzyme is attached to a carrier which is chemically relatively resistant or inert, partially or unrestrictedly resistant to microorganisms, possesses favorable mechanical properties and ensures high flow velocity. It is a further requirement that the enzyme should be bound onto the carrier under mild reaction conditions.

It has been found that the following carrier fully comply with the above requirements:
(a) polysacharide derivatives which comprise primary amino group and contain at least 0.1 m-equiv./g —preferably 1-2 m-equiv./g of functional —NH$_2$ group;
(b) polymers produced from acrylic acid and/or methacrylic acid or acrylamide and/or methacrylamide monomer by means of a cross-linking agent of the acrylic or allylic type (e.g. N,N'-methylene-bis-acrylic amide, ethylene diacrylate or N,N'-diallyl-tartaric amide which contain at least 0.1 m-equiv./g—preferably 2–8 m-equiv./g—of functional —COOH group.

In the case of polysaccharide carriers comprising primary amino group the carboxy groups of certain aspartyl or glutamyl side-chains of the enzyme are converted by treatment with a carbodiimide into a O-acyl-isourea derivative which reacts with the amino groups of the carrier. In the case of polymeric carriers comprising functional carboxy groups the said carboxy groups are activated by treatment with a carbodiimide by methods known per se and are thus made suitable for binding the CGTase enzyme. The use of a carbodiimide as activating agent is advantageous since the activation reaction can be carried out under mild conditions (0°–4° C., pH 6.0–8.0).

According to the invention there is provided a process for the immobilization of cyclodextrin glycosyltransferase enzyme which comprises
(a) activating a cyclodextrin glycosyltransferase enzyme with a carbodiimide compound which is water-soluble or soluble in an organic solvent at a temperature below 0° C., and thereafter applying the thus treated enzyme in a solution having a pH value of 4.5–8.5 onto a derivative of a polysacharide comprising at least 0.1 m-equiv./g of —NH$_2$ group, and washing and if desired drying the product; or
(b) activating a polymer group comprising at least 0.1 mequiv./g. of functional —COOH group produced from an acrylic acid and/or methacrylic acid or acrylic amide and/or methacrylic amide monomer by means of a cross-linking agent of the acrylic or allylic type with a carbodiimide compound being water-soluble or soluble in an organic solvent at a temperature below 0° C. and thereafter applying a cyclodextrine glycosyl transferase enzyme in a solution having a pH-value of 4.5 to 8.5 onto the thus activated polymer, and washing and, if desired, drying the product.

As the polymer preferably aminopropyl derivatives of cellulose or dextrans can be used (CELLULOSE A ™ MOL-SECT A ™) but acrylamide-N,N'-methylene-bis-acrylamide-acrylic acid copolymers (AKRILEX C) can be employed as well.

In the process of the present invention a CGTase enzyme of any origin isolated by any known method can be used.

As activating carbodiimide compound e.g. N-cyclohexyl-N'-[2-(4-morpholinyl)-ethyl]-carbodiimide-methyl-p-toluene sulfonate or N-ethyl-N'-(3-dimethylaminopropyl)-carbodiimide-hydrochloride can be used. It is preferred to use water soluble carbodiimides. From the carbodiimides soluble only in organic solvents only those compounds can be used which are soluble in cold organic solvents (i.e. at a temperture below 0° C.).

The CGTase or the O-acyl-isourea derivative thereof can be applied on the carrier from a solution having a pH between 4.5 and 8.5—preferably 6.5. As the reaction medium preferably a 0.05–0.1 molar sodium acetate buffer solution having a pH of 6.5 can be used.

The immobilized enzyme composition prepared by the coupling reaction is washed in a known manner and if desired dried. The enzyme compositions can also be stored at 0°–4° C. in an aqueous suspension.

The activity of the immobilized enzyme compositions prepared by the present invention mount to 13–450 Kitahata units/g xerogel, which is very favorable from the point of view of practical use. (1 unit corresponds to an enzyme amount which induces at 40° C. a linear transmission increase of 1% per minute).

The CGTase enzyme composition immobilized on acrylamide-N,N'-methylene-bis-acrylamide-acrylic acid AKRILEX C ™ by the process of the present invention shows in a mildly acidic medium (i.e. at the optimal pH of use, at pH 5.5) a greater stability than the dissolved enzyme. This advantage is particularly important when the enzyme composition is used for a longer period of time. The immobilization reaction preferably takes 45-55 hours and more preferably 48 hours.

SPECIFIC EXAMPLES

Further details of the present invention are to be found in the following Examples without limiting the scope of protection to the said Examples.

The following examples 1-11 designate the starting resin material used to immobilize the enzymes by trademark rather than by chemical composition. The following material will serve to define the meaning of the trademarks.

(1) CELLULOSE A TM is an aminopropyl derivative of cellulose; its preparation is described in Hungarian Pat. No. 180,285.

(2) MOLSELECT A TM is an aminopropyl derivative of dextrose; its preparation is also described in Hungarian Pat. No. 180,285.

(3) AKRILEX C 100 XEROGEL TM is a polymer comprising acryl amide, N,N'-methylene-bis-acryl amide and acrylic acid units; its preparation is described in Hungarian Pat. No. 183,171. The preparation of AKRILEX C 100 XEROGEL TM through the hydrolysis of AKRILEX P TM is described in U.S. patent application Ser. No. 486,286 (allowed 19 June 1985).

(4) AKRILEX AH-C$_4$ TM is a succinic acid derivative of a polymer comprising acryl amide, N,N'-methylene-bis-acrylamide and acrylic acid hydrazide units; its preparation comprises subjecting a polyacrylamide being cross-linked with N,N'-methylene-bis-acryl amide (this is the polymer AKRILEX P TM) to hydrazinolysis and treating the thus-obtained product with succinic acid anhydride. The starting AKRILEX P TM polymer is described in U.S. Pat. No. 4,532,214 and in U.S. patent application Ser. No. 486,286, mentioned above.

EXAMPLE 1

To 3 g of a carrier of the CELLULOSE A TM type (dry substance content 17%; binding capacity —NH$_2$ content—1.86 m-equiv./g/ 55 ml of a salt-fre CGTase solution (protein content 9.9 mg/ml) are added. For the solubilization and dialysis of the enzyme a 0.05 molar sodium acetate buffer (pH 6.5) is used. The mixture is stirred on an icecold water-bath for 10 minutes, whereupon a solution of 1 g of N-cyclohexyl-N'-[2-(4-morpholinyl)-ethyl]-carbodiimide-methyl-p-toluene-sulfonate in 20 ml of cold (+4° C.) buffer is added. The reaction is carried out at 0°-4° C. for 48 hours and during this period the reaction mixture is stirred twice for 6 hours each. The solid phase is separated by filtration and washed three times with 60 ml of a sodium acetate buffer each (pH 6.5), three times with 60 ml of a 0.05 molar sodium acetate buffer each comprising 1 mole of sodium chloride (pH 6.5) and three times with 60 ml of a 0.05 mole sodium acetate buffer each (pH 6.5). The product is washed finally salt-free three times with 120 ml of distilled water each. The product is filtered off, suspended in 40 ml of a 0.05 molar sodium acetate buffer (pH 6.5) and stored in a refrigerator at +4° C. Thus 758 mg of immobilized CGTase (related to dry substance) are obtained. Activity: 26.5 Kithata units/g dry substance.

EXAMPLE 2

To 1.5 g of a carrier of the MOLSELECT A TM type (dry substance content 33%; binding capacity-NH$_2$ content—1.27 m-equiv./g) 55 ml of a salt-free CGTase solution (protein content 9.8 mg/ml) are added. For the solubilisation and dialysis of the enzyme a 0.05 molar sodium acetate buffer (pH 6.5) is used. The mixture is stirred on an ice-cold water-bath for 10 minutes, whereupon a solution of 0.5 g of N-cyclohexyl-N'-[2-(4-morpholinyl)-ethyl]-carbodimide-methyl-p-toluene-sulfonate in 5 ml of cold (+4° C.) buffer is added. The reaction is carried out at 0-4° C. for 48 hours and during this period the reaction mixture is stirred twice for 6 hours each. The solid phase is separated by filtration and washed three times with 60 ml of a sodium acetate buffer each (pH 6.5), three times with 60 ml of a 0.05 molar sodium acetate buffer each comprising 1 mole of sodium chloride (pH 6.5) and three times with 60 ml of a 0.05 mole sodium acetate buffer each (pH 6.5). The product is washed finally salt-free twice with 120 ml of distilled water each. The product is filtered off, suspended in 40 ml of a 0.05 molar sodium acetate buffer (pH 6.5) and stored in a refrigerator at +4° C. Thus 861 mg of immobilized CGTase (related to dry substance) are obtained. Activity: 13.6 Kitahata units/g dry substance.

EXAMPLE 3

0.4 g of an AKRILEX AH-C$_4$ TM xerogel (binding capacity—COOH content—3.08 m-equiv./g) are suspended in 8 ml of a 0.05 molar sodium acetate buffer (pH 6.5) whereupon on an icecold water-bath under constant sitrring a solution of 0.8 g of N-cyclohexyl-N'[2-(4-morpholinyl)-ethyl]-carbodiimide-methyl-p-toluene-sulfonate in 10 ml of a cold (+4° C.) buffer is added. The reaction mixture is stirred for 10 minutes whereupon 40 ml of a CGTase solution (10 mg/ml) are added. For the solubilization and dialysis of the enzyme a 0.05 molar sodium acetate buffer (pH 6.5) is used. At 0°-4° C. the total reaction time amounts to 48 hours and during this period the reaction mixture is stirred twice for 6 hours each. The gel is separated by filtration and washed three times with 50 ml of a 0.05 molar sodium acetate buffer each (pH 6.5), three times with 100 ml of a 0.05 molar sodium acetate buffer (pH 6.5) each comprising 1 mole of sodium chloride and twice with 100 ml of a 0.05 molar sodium acetate buffer (pH 6.5) each. The gel is finally washed salt-free twice with 250 ml of distilled water each and lyophilized. Thus 0.2 g of immobilized CGTase enzyme are obtained. Activity: 80 Kitahata units/g xerogel.

EXAMPLE 4

0.13 g of an AKRILEX C 100 XEROGEL TM (binding capacity —COOH content—6.2 m-equiv./g; particles size 100-320 μm) is suspended in 5 ml of a 0.05 molar sodium acetate buffer (pH 0.5), whereupon at 0° C. under constant stirring a solution of 0.25 g of N-cyclohexyl-N'[2-(4-morpholinyl)-ethyl]-carbodiimide-methyl-p-toluene-sulfonate in 5 ml of a cold (+4° C.) 0.05 molar sodium acetate buffer (pH 5.0) is added. The reaction mixture is stirred for 10 minutes, whereupon 11 ml of a CGTase solution (11.4 mg/ml) are added and the pH of the reaction mixture is adjusted to 5.0. At 0°-4° C. the total reaction time amounts to 48 hours and during this period the suspension is stirred twice for 6 hours each. At the beginning of the reaction the pH is controlled every half an hour and later once an hour and if necessary red-adjusted. The reaction having been completed the gel is removed by centrifugation and washed three times with 30 ml of a 0.05 molar sodium acetate buffer (pH 5.0) each, three times with 30 ml of a 0.05 molar sodium acetate buffer (pH 5.0) each comprising 1 mole of sodium chloride and three times with 30 ml of a 0.05 molar sodium acetate buffer (pH 5.0) each. The gel is finally washed salt-free three times with 60 ml of distilled water and nophilized. Thus 0.2 g of immobilized CGTase are obtained. Activity: 147 Kitahata units/g xerogel.

EXAMPLE 5

0.13 g AKRILEX C-100 XEROGEL ™ (binding capacity —COOH content—6.2 m-equiv./g; particles size 100–320 μm) is suspended in 5 ml of a 0.05 molar sodium acetate buffer (pH 5.5), whereupon at 0° C. under constant stirring a solution of 0.25 g of N-cyclohexyl-N'-[2-(4-morpholinyl)-ethyl]-carbodiimide-methyl-p-toluene-sulfonate in 5 ml of a cold (+4° C.) 0.05 molar sodium acetate buffer (pH 5.5) is added. The reaction mixture is stirred for 10 minutes, whereupon 11 ml of a CGTase solution (11.4 mg/ml) are added and the pH of the reaction mixture is adjusted to 5.5. A 0°–4° C. the total reaction time amounts to 48 hours and during this period the suspension is stirred twice for 6 hours each. At the beginning of the reaction the pH is controlled every half an hour and later once an hour and if necessary re-adjusted. The reaction having been completed the gel is removed by centrifugation and washed three times with 30 ml of a 0.05 molar sodium acetate buffer (pH 5.5) each, three times with 30 ml of a 0.05 molar sodium acetate buffer (pH 5.5) each comrpising 1 mole of sodium chloride and three times with 30 ml of a 0.05 molar sodium acetate buffer (pH 5.5) each. The gel is finally washed salt-free three times with 60 ml of distilled water and lyophilized. Thus 0.2 g of immobilized CGTase are obtained. Activity: 235 Kitahata units/g xerogel.

EXAMPLE 6

0.13 g of an AKRILEX C 100 XEROGEL ™ (binding capacity—COOH content—6.2 m-equiv./g; particles size 100–320 μm) is suspended in 5 ml of a 0.05 molar sodium acetate buffer (pH 6.0), whereupon at 0° C. under constant stirring a solution of 0.26 g of N-cyclohexyl-N'-[2-(4-morpholinyl)-ethyl]-carbodiimide-methyl-p-toluene-sulfonate in 5 ml of a cold (+4° C.) 0.05 molar sodium acetate buffer (pH 6.0) is added. The reaction mixture is stirred for 10 minutes, whereupon 13 ml of a CGTase solution (10 mg/ml) are added and the pH of the reaction mixture is adjusted to 6.0. At 0°–4° C. the total reaction time amounts to 48 hours and during this period the suspension is stirred twice for 6 hours each. At the beginning of the reaction the pH is controlled every half an hour and later once an hour and if necessary re-adjusted. The reaction having been completed the gel is removed by centrifugation and washed three times with 30 ml of a 0.05 molar sodium acetate buffer (pH 6.0) each, three times with 30 ml of a 0.05 molar sodium acetate buffer (pH 6.0) each comprising 1 mole of sodium chloride and three times with 30 ml of a 0.05 molar sodium acetate buffer (pH 6.0) each. The gel is finally washed salt-free three times with 60 ml of distilled water and lyophilized. Thus 0.2 g of immobilised CGTase are obtained. Activity: 380 Kitahata units/g xerogel.

EXAMPLE 7

0.13 g of an AKRILEX C 100 XEROGEL ™ (binding capacity—COOH content—6.2 m-equiv./g; particles size 100–320 μm) is suspended in 5 ml of a 0.05 molar sodium acetate buffer (pH 6.5), whereupon at 0° C. under constant stirring a solution of 0.26 g of N-cyclohexyl-N'-[2-(4-morpholinyl)-ethyl]-carbodiimide-methyl-p-toluene-sulfonate in 5 ml of a cold (+4° C.) 0.05 molar sodium acetate buffer (pH 6.5) is added. The reaction mixture is stirred for 10 minutes, whereupon 13 ml of a CGTase solution (10 mg/ml) are added and the pH of the reaction mixture is adjusted to 6.5. At 0°–4° C. the total reaction time amounts to 48 hours and during this period the suspension is stirred twice for 6 hours each. At the beginning of the reaction the pH is controlled every half an hour and later once an hour and if necessary re-adjusted. The reaction having been completed the gel is removed by centrifugation and washed three times with 30 ml of a 0.05 molar sodium acetate buffer (pH 6.5) each, three times with 30 ml of a 0.05 molar sodium acetate buffer (pH 6.5) each comprising 1 mole of sodium chloride and three times with 30 ml of a 0.05 molar sodium acetate buffer (pH 6.5) each. The gel is finally washed salt-free three times with 60 ml of distilled water and lyophilized. Thus 0.2 g of immobilized CGTase are obtained. Activity: 450 Kitahata units/g xerogel.

EXAMPLE 8

1 g AKRILEX C-100 XEROGEL ™ (binding capacity—COOH content—6.2 m-equiv./g; particles size 100–320 μm) is suspended in 24 ml of a 0.05 molar sodium acetate buffer (pH 7.0), whereupon at 0° C. under constant strring a solution of 2 g of N-cyclohexyl-N'-[2-(4-morpholinyl)-ethyl]-carbodiimide-methyl-p-toluene-sulfonate in 15 ml of a cold (+4° C.) 0.05 molar sodium acetate buffer (pH 7.0) is added. The reaction mixture is stirred for 10 minutes, whereupon 113 ml of a CGTase solution (12 mg/ml) are added and the pH of the reaction mixture is adjusted to 7.0. At 0°–4° C. the total reaction time amounts to 48 hours and during this period the suspension is stirred twice for 6 hours each. At the beginning of the reaction the pH is controlled every half an hour and later once an hour and if necessary re-adjusted. The reaction having been completed the gel is removed by centrifugation and washed three times with 300 ml of a 0.05 molar sodium acetate buffer (pH 7.0) each, three times with 300 ml of a 0.05 molar sodium acetate buffer (pH 7.0) each comprising 1 mole of sodium chloride and three times with 300 ml of a 0.05 molar sodium acetate buffer (pH 7.0) each. The gel is finally washed salt-free three times with 300 ml of distilled water and lyophilized. Thus 1.5 g of immobilized CGTase are obtained. Activity: 366 Kitahata units/g xerogel.

EXAMPLE 9

0.2 g AKTILEX C-100 XEROGEL ™ (binding capacity—COOH content—6.2 m-equiv./g; particles size 100–320 μm) is suspended in 5 ml of a 0.05 molar sodium acetate buffer (pH 7.5), whereupon at 0° C. under constant stirring a solution of 0.4 g of N-cyclohexyl-N'-[2-(4-morpho-ethyl]-carbodiimide-methyl-p-toluene-sulfonate in 5 ml of a cold (+4° C.) 0.05 molar sodium acetate buffer (pH 7.5) is added. The reaction mixture is stirred for 10 minutes, whereupon 21.6 ml of a CGTase solution (12 mg/ml) are added and the pH of the reaction mixture is adjusted to 7.5. At 0°–4° C. the total reaction time amounts to 48 hours and during this period the suspension is stirred twice for 6 hours each. At the beginning of the reaction the pH is controlled every half an hour and later once an hour and if necessary re-adjusted. The reaction having been completed the gel is removed by centrifugation and washed three times with 60 ml of a 0.05 molar sodium acetate buffer (pH 7.5) each, three times with 60 ml of a 0.05 molar sodium acetate buffer (pH 7.5) each comprising 1 mole of sodium chloride and three times with 60 ml of a 0.05 molar sodium acetate buffer (pH 7.5) each. The gel is finally washed salt-free twice with 200 ml of distilled water and lyophilized. Thus 0.3 g of immobilized CGTase are obtained. Activity: 370 Kitahata units/g xerogel.

EXAMPLE 10

0.26 g AKRILEX C-100 XEROGEL TM (binding capacity—COOH content—6.2 m -equiv./g; particles size 100–320 μm) is suspended in 10 ml of a 0.05 molar sodium acetate buffer (pH 8.0), whereupon at 0° C. under constant stirring a solution of 0.52 g of N-cyclohexyl-N'-[2-(4-morpholinyl)-ethyl]-carbodiimide-methyl-p-toluene-sulfonate in 10 ml of a cold (+4° C.) 0.05 molar sodium acetate buffer (pH 8.0) is added. The reaction mixture is stirred for 10 minutes, whereupon 29 ml of a CGTase solution (9.25 mg/ml) are added and the pH of the reaction mixture is adjusted to 8.0. At 0°–4° C. the total reaction time amounts to 48 hours and during this period the suspension is stirred twice for 6 hours each. At the beginning of the reaction the pH is controlled every half an hour and later once an hour and if necessary re-adjusted. The reaction having been completed the gel is removed by centrifugation and washed three times with 60 ml of a 0.05 molar sodium acetate buffer (pH 8.0) each, three times with 60 ml of a 0.05 molar sodium acetate buffer (pH 8.0) each comprising 1 mole of sodium chloride and three times with 60 ml of a 0.05 molar sodium acetate buffer (pH 8.0) each. The gel is finally washed salt-free twice with 200 ml of distilled water and lyophilized. Thus 0.3 g of immobilized CGTase are obtained. Activity: 300 Kitahata units/g xerogel.

EXAMPLE 11

0.26 g AKRILEX C-100 XEROGEL TM/binding capacity—COOH content—6.2 m-equiv./g; particles size 100–320 μm) is suspended in 10 ml of a 0.05 molar sodium acetate buffer (pH 8.5), whereupon at 0° C. under constant stirring a solution of 0.52 g of N-cyclohexyl-N'-[2-(4-)-morpholinyl)-ethyl]-ethyl]-carbodiimide-methyl-p-toluene-sulfonate in 10 ml of a cold (+4 °C) 0.05 molar sodium acetate buffer (pH 8.5) is added. The reaction mixture is stirred for 10 minutes, whereupon 29 ml of a CGTase solution (9.25 mg/ml) are added and the pH of the reaction mixture is adjusted to 8.5. At 0°–4° C. the total reaction time amounts to 48 hours and during this period the suspension is stirred twice for 6 hours each. At the beginning of the reaction the pH is controlled every half an hour and later once an hour and if necessary re-adjusted. The reaction having been completed the gel is removed by centrifugation and washed three times with 60 ml of a 0.05 molar sodium acetate buffer (pH 8.5) each, three times with 60 ml of a 0.05 molar sodium acetate buffer (pH 8.5) each comprising 1 mole of sodium chloride and three times with 60 ml of a 0.05 molar sodium acetate buffer (pH 8.5) each. The gel is finally washed salt-free twice with 200 ml of distilled water and lyophilized. Thus 0.4 g of immobilized CGTase are obtained. Activity: 173 Kitahata units/g xerogel.

TABLE 1

| | Immobilization of cyclodextrin glycosyltransferase | | | | |
|---|---|---|---|---|---|
| Carrier | Immobilized protein /%/ | Immobilized activity /%/ | Activity recovered in dissolved form /%/ | Loss of activity /%/ | Activity of product /Kitahata units/g dry substance/ |
| Cellulose A | 26.8 | 0.1 | 6.4 | 93.5 | 26.5 |
| Molselect A | 26.9 | 0.1 | 13.5 | 86.4 | 13.6 |
| Akrilex AH-C$_4$ | 27.9 | 0.1 | 11.5 | 88.4 | 80.0 |
| Akrilex C-100 | 39.4 | 3.84 | 63.0 | 33.16 | 450.0 |

TABLE 2

| | Effect of pH value on the immobilization of cyclodextrin glycosyltransferase enzyme on Akrilex C carrier | | | | |
|---|---|---|---|---|---|
| pH of reaction mixture | Immobilized protein /%/ | Immobilized activity /%/ | Activity recovered in dissolved form /%/ | Loss of activity /%/ | Activity of product /Kitahata units/g xerogel/ |
| 5.0 | 36.6 | 0.75 | 38.9 | 60.35 | 147 |
| 5.5 | 26.0 | 1.20 | 40.0 | 58.80 | 235 |
| 6.0 | 36.0 | 3.25 | 78.0 | 18.75 | 380 |
| 6.5 | 39.4 | 3.84 | 63.0 | 33.16 | 450 |
| 7.0 | 47.4 | 1.83 | 41.0 | 57.17 | 366 |
| 7.5 | 48.8 | 1.93 | 73.0 | 25.07 | 370 |
| 8.0 | 52.0 | 0.50 | 43.0 | 56.50 | 300 |
| 8.5 | 53.5 | 0.39 | 50.6 | 49.01 | 173 |

What we claim is:
1. A process for the immobilization of cyclodextrin glycosyl transferase enzyme which comprises the steps of:
    (a) activating a cyclodextrin glycosyl transferase enzyme either in an aqueous solution with a carbodiimide compound that is water-soluble, at a temperature of 0° to 4° C. or in an organic solvent with a carbodiimide compound that is soluble in an organic solvent, at a temperature less than 0° C; and
    (b) immobilizing the enzyme by applying the enzyme treated according to step (a) in an aqueous buffer solution having a pH value between 4.5 and 8.5 onto a carrier which is a derivative of a polysac- charide compound comprising at least 0.1 m. equiv. of —NH₂ groups per gram of carrier, and washing the product.

2. The process defined in claim 1, wherein the carrier in step (b) which contains —NH₂ groups is an aminopropyl derivative of cellulose or dextran.

3. The process defined in claim 1, wherein in step (a) the carbodiimide compound is N-cyclohexyl-N'-[2-(4-morpholinyl)-ethyl]-carbodiimide-methyl-p-toluene-sulfonate or N-ethyl-N'-(3-dimethylaminopropyl)-carbodiimide hydrochloride.

4. The process defined in claim 1, wherein in step (b) the immobilization is carried out in a 0.05 to 0.1 molar sodium acetate buffer solution having a pH value of 6.5.

5. The process defined in claim 1, wherein in step (b) the immobilization is carried out for 45–55 hours.

6. The process defined in claim 1, wherein in step (b) the immobilization enzyme is first washed with a sodium acetate buffer, then with a sodium acetate buffer also containing sodium chloride, and then with distilled water.

7. A process for the immobilization of cyclodextrin glycosyl transferase enzyme which comprises the steps of:

(a) activating a polymer carrier comprising at least 0.1 m. equiv. of functional —COOH groups per gram of carrier, said polymer carrier having been produced from an acrylic acid and/or methacrylic acid, or acrylic amide and/or methacrylic amide monomer, and a cross-linking agent of the acrylic or allylic type either in an aqueous solution with a carbodiimide compound that is water soluble, at a temperature of 0° to 4° C. or in an organic solvent with a carbodiimide compound that is soluble in an organic solvent, at a temperature less than 0° C; and (b) applying a cyclodextrin glycosyl transferase enzyme in an aqueous buffer solution having a pH value of 4 to 9 onto the polymer carrier to immobilize the enzyme, and washing the product.

8. The process defined in claim 9, wherein the polymer carrier in step (a) comprising functional —COOH groups is an acrylamide-N,N'-methylene-bis-acrylamide-acrylic acid copolymer.

9. The process defined in claim 7, wherein in step (a), the carbodiimide compound is N-cyclohexyl-N'-[2-(4-morpholinyl)-ethyl]-carbodiimide-methyl-p-toluene-sulfonate or N-ethyl-N' (3-dimethylaminopropyl)-carbodiimide hydrochloride.

10. The process defined in claim 7, wherein in step (b) the immobilization is carried out in a 0.05 to 0.1 molar sodium acetate buffer solution having a pH value of 6.5.

11. The process defined in claim 7, wherein in step (b) the immobilization is carried out for 45–55 hours.

12. The process defined in claim 7, wherein in step (b), the immobilized enzyme is first washed with a sodium acetate buffer, then with a sodium acetate buffer also containing sodium chloride, and then with distilled water.

* * * * *